United States Patent [19]

Heller

[11] Patent Number: 4,980,089
[45] Date of Patent: Dec. 25, 1990

[54] PHOTOCHROMIC SPIROPYRAN COMPOUNDS

[75] Inventor: Harry G. Heller, Cardiff, Wales

[73] Assignee: PPG Industries, Inc., Pittsburgh, Pa.

[21] Appl. No.: 378,945

[22] Filed: Jul. 12, 1989

[51] Int. Cl.$^5$ ...................... G02B 5/23; C07D 311/96
[52] U.S. Cl. .................................... 252/586; 549/331; 544/70; 350/359; 523/106; 351/163
[58] Field of Search ................ 252/586; 549/408, 389, 549/390, 381, 406, 331, 384; 351/163; 544/70; 350/339; 523/106

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 4,010,286 | 3/1977 | Hall et al. | 426/536 |
| 4,215,010 | 7/1980 | Hovey et al. | 252/300 |
| 4,238,501 | 12/1980 | Kabbe et al. | 424/283 |
| 4,342,668 | 8/1982 | Hovey et al. | 252/586 |
| 4,503,177 | 3/1985 | Reid et al. | 524/87 |
| 4,563,458 | 1/1986 | Widdig et al. | 514/253 |
| 4,637,698 | 1/1987 | Kwak et al. | 351/163 |
| 4,826,977 | 5/1989 | Heller et al. | 544/70 |

FOREIGN PATENT DOCUMENTS

| | | |
|---|---|---|
| 246114 | 5/1987 | European Pat. Off. |
| 250193 | 6/1987 | European Pat. Off. |
| 294056 | 12/1988 | European Pat. Off. |

OTHER PUBLICATIONS

Mazza, S. M. et al, J. Org. Chem. 53, 3681, 1988.
Padwa et al, J. Org. Chem., vol. 40, No. 8, 1975, 1142.

*Primary Examiner*—John S. Maples
*Assistant Examiner*—Richard Treanor
*Attorney, Agent, or Firm*—Irwin M. Stein

[57] ABSTRACT

Described are a series of novel benzospiropyran and naphthospiropyran compounds in which a norcamphor group (or its alkyl-substituted homologues) or a tricyclodecane group (or its alkyl-substituted derivatives) are appended at the 2-position of the benzospiropyran or naphthospiropyran ring. Also described are organic host materials that contain or that are coated with materials containing such compounds. Articles, such as ophthalmic or plano lenses, that incorporate the novel pyran compounds or combinations of the novel pyran compounds with other complementary photochromic compounds are described.

30 Claims, No Drawings

PHOTOCHROMIC SPIROPYRAN COMPOUNDS

DESCRIPTION OF THE INVENTION

The present invention relates to certain novel benzospiropyran and naphthospiropyran compounds. More particularly, this invention relates to novel photochromic benzospiropyran and naphthospiropyran compounds, and to compositions and articles containing such novel spiropyran compounds. When exposed to light radiation involving ultraviolet rays such as the ultraviolet radiation in sunlight or the light of a mercury lamp, a photochromic compound changes color. If the ultraviolet radiation is discontinued, the photochromic compound will return to its original color.

Various classes of photochromic compounds have been synthesized and suggested for use in applications in which a sunlight-induced color change or darkening is desired. U.S. Pat. No. 3,567,605 (Becker) describes a series of pyran derivatives, including certain benzopyrans and naphthopyrans, which exhibit photochromic properties. These compounds are described as derivatives of chromene and are reported to undergo a color change, e.g., from colorless to yellow-orange, on irradiation by ultraviolet light at temperatures below about $-40°$ C. Irradiation of the compounds with visible light or upon raising the temperature to within the range of $-10°$ C. to $0°$ C. is reported to reverse the coloration to a colorless state. U.S. Pat. No. 4,563,458 describes certain 2H-chromenes as precursors of certain chroman-4-aldehydes, which are reacted with certain amines to prepare 4-aminomethylene-chromans and -chromenes that are used in medicaments.

European Patent Publication 246,114 describes a series of photochromic spiropyrans in which an adamantane group is attached at the 2-position of the benzopyran or naphthopyran ring. European Patent Publication 250,193 describes photoreactive plastic lenses that are coated or impregnated with the photochromic spiropyrans of European Patent Publication 246,114 in combination with a blue photochromic benzopyran or naphthopyran having an aminophenyl substituent at the 2-position of the pyran ring.

Padwa et al in J. Org. Chem., Volume 40, No. 8, 1975, page 1142, describes the investigation of photochemical reactions of 2,2-dimethylbenzopyran and related compounds, identifies the by-products and suggests pathways to the ring-opened color intermediates and the final non-colored phenolics. The color forms examined by the authors are reported as being unstable at room temperature. The authors do not suggest ways in which the stability of the examined compounds might be improved, nor any modification that might be made to the structure of the known pyran compounds.

It has now been discovered that certain novel benzospiropyran and naphthospiropyran compounds containing a norcamphor group (or its alkyl-substituted homologues) or a tricyclodecane group at the 2-position of the benzospiropyran or naphthospiropyran ring can be prepared. These compounds have been found to exhibit photochromic properties.

DETAILED DESCRIPTION OF THE INVENTION

In accordance with the present invention, there are provided novel benzospiropyran and naphthospiropyran compounds that may be graphically represented by the following graphic formulae, wherein graphic formula I is representative of the norcamphor-substituted benzospiropyran series, graphic formulae II and III represent the alpha and beta norcamphor-substituted naphthospiropyran isomers respectively, and graphic formulae IV-a and IV-b represent the alpha and beta tricyclodecane-substituted naphthospiropyran isomers respectively. In addition, the bridge carbon atom of the aforedescribed benzo- or naphthospiropyrgan compounds may face toward the ring oxygen or toward the double bond between the number 3 and 4 carbon atoms in the pyran ring, thereby giving rise to two structural isomers for each of the colorless forms. Such a structural isomer from the compounds of graphic formula I may be depicted in graphic formula I'. Similar structural isomers for the naphthospiropyrans of graphic formulae II—IV may also be drawn. For purposes of the present description and the accompanying claims, graphic formulae I-IV shall be deemed to include all structural isomers of the depicted compounds.

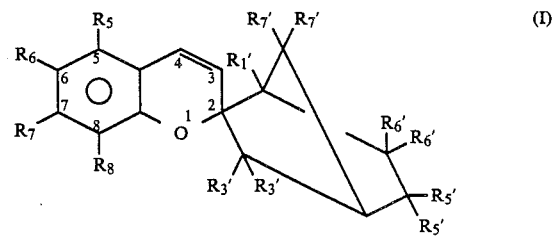

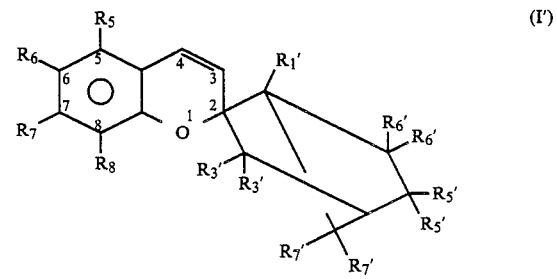

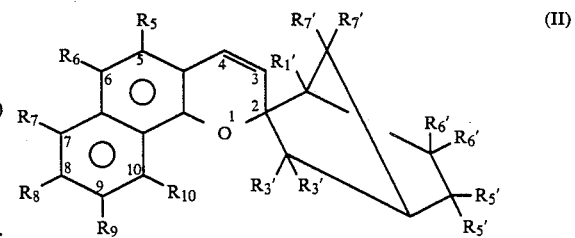

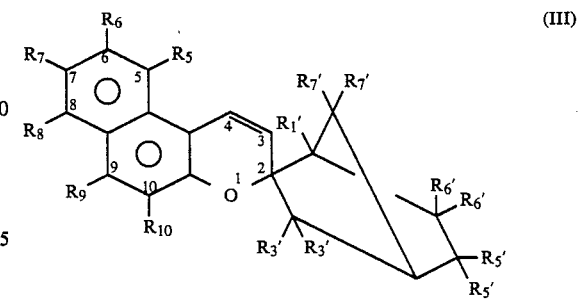

-continued

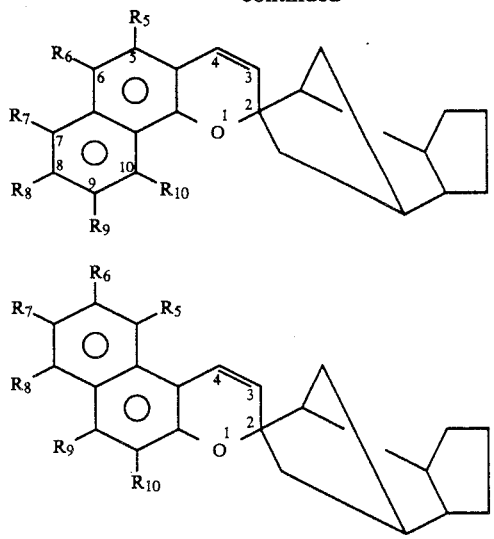

A variety of substituents may be placed on the benzo and naphtho portions of the benzospiropyran and naphthospiropyran rings. For example, such rings may be substituted in the positions represented respectively by $R_5$–$R_8$ in graphic formula I and $R_5$–$R_{10}$ in graphic formulae II–IV with $C_1$–$C_{10}$ straight and branched chain alkyl, $C_5$–$C_7$ cycloalkyl, phenyl, mono- or di-substituted phenyl, $C_1$–$C_4$ alkoxy, halogen, i.e. chlorine, fluorine, bromine and iodine, and five or six-membered heterocyclic groups connected to the benzospiropyran or naphthospiropyran rings by a single bond, e.g., furyl and thienyl. More particularly, $R_5$–$R_{10}$ may be $C_1$–$C_5$ alkyl, e.g., methyl, ethyl, n-propyl, isopropyl, butyl, and pentyl, $C_5$–$C_6$ cycloalkyl, e.g., cyclopentyl and cyclohexyl, $C_1$–$C_3$ alkoxy, e.g., methoxy, ethoxy and propoxy, the halogens [chlorine (chloro) and bromine (bromo)], 2- or 3- furyl, 2- or 3- thienyl, phenyl, and ortho-, meta- or para-substituted phenyl. The aforedescribed phenyl substituent(s) may be selected from the group consisting of $C_1$–$C_4$ alkyl ($C_1$–$C_4$ alkylphenyl), $C_1$–$C_4$ alkoxy ($C_1$–$C_4$ alkoxyphenyl), chloro and bromo. Preferably, the phenyl group is substituted with one substituent and that substituent is in the para position, e.g., p-methyl phenyl, p-chloro phenyl and p-methoxy phenyl. Still more particularly, $R_5$–$R_{10}$ may be $C_1$–$C_3$ alkyl, $C_1$–$C_3$ alkoxy, e.g., methoxy, ethoxy and propoxy, the halogens [chlorine (chloro) and bromine (bromo)], phenyl and $C_1$–$C_3$ alkoxyphenyl, e.g., p-methoxy phenyl. When any of the positions represented by $R_5$–$R_{10}$ of the benzospiropyran and naphthospiropyrans are not substituted with one of the aforementioned substituent groups, such unsubstituted $R_5$–$R_{10}$ positions are hydrogen.

In naming and referring to the benzospiropyran and naphthospiropyran compounds of graphic formulae I–IV, positions on the rings are numbered counterclockwise starting with the oxygen atom as number (1). Such positions are indicated by the numbers appearing on the inside of the rings depicted in graphic formulae I–IV. As shown in graphic formula I, the benzospiropyran ring may be substituted at the 5, 6, 7 and/or 8 positions, i.e., $R_5$, $R_6$, $R_7$ and/or $R_8$. When not substituted, $R_5$–$R_8$ are hydrogen. In certain embodiments, the benzospiropyran ring is substituted at the 5- position, or the 5- and 8-positions, i.e., $R_5$, or $R_5$ and $R_8$. In such respective embodiments, $R_6$–$R_8$ or $R_6$ and $R_7$ are each hydrogen.

As shown in graphic formulae II–IV, the naphthospiropyran ring may be substituted at the 5, 6, 7, 8, 9 and/or 10 position, i.e., $R_5$–$R_{10}$. When not so substituted, $R_5$–$R_{10}$ are hydrogen. In certain embodiments, the naphthospiropyran ring is substituted at the 5-position, at the 5- and 6-positions, or the 5- and 9-positions, i.e., $R_5$, $R_5$ and $R_6$, or $R_5$ and $R_9$. In such embodiments, $R_6$–$R_{10}$, $R_7$–$R_{10}$ or $R_6$–$R_8$ and $R_{10}$ are respectively each hydrogen.

The norcamphane group (and its alkyl homologues) attached to the 2-position of the pyran moiety may be represented by the following graphic formula V:

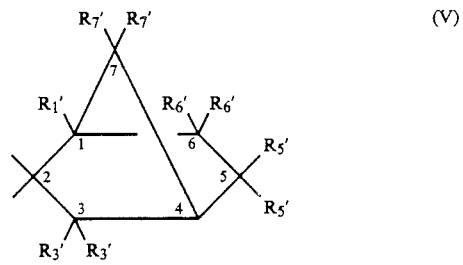

In graphic formula V, numbering of the carbon atoms of the norcamphor group are illustrated by the numbers 1–7 within the methylene bridged bicyclic group. To distinguish it from the carbon atoms of the pyran moiety, the R numbered substituents of the norcamphane group are designated with a prime ('). The norcamphane is attached to the pyran moiety at the number 2 carbon atom, which attachment is illustrated by the two bond lines emanating from that carbon atom.

The $R_1'$ and $R_3'$ substituents may be selected from the group consisting of hydrogen and $C_1$–$C_5$ alkyl, e.g., methyl, ethyl, propyl, butyl and pentyl, preferably, methyl. $R_5'$, $R_6'$ and $R_7'$ may be selected from hydrogen and methyl ($C_1$ alkyl). When $R_1'$ is hydrogen, $R_3'$, $R_5'$, $R_6'$ and $R_7'$ are each hydrogen, and when $R_1'$ is alkyl, e.g., methyl, one of the substituents $R_3'$, $R_5'$, $R_6'$ and $R_7'$ is methyl, the remaining substituents of the group $R_3'$, $R_5'$, $R_6'$ and $R_7'$ being hydrogen. Preferably, the alkyl substituents are methyl. The bicyclic norcamphane group (and its alkyl derivatives) may be described as derivatives of norcamphor, which may be represented by graphic formula VI:

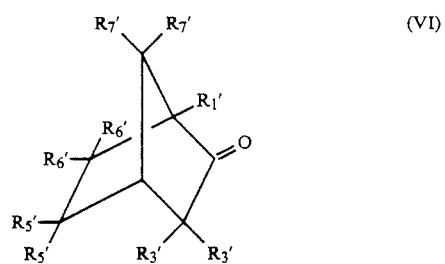

When all of the $R_1'$, $R_3'$, $R_5'$, $R_6'$ and $R_7'$ substituents are hydrogen, the bicyclic compound of graphic formula VI is known as norcamphor. When $R_1'$ and $R_3'$ are methyl, the compound is known as fenchone. Similarly, when $R_1'$ are $R_5'$ methyl, the compound is termed isofenchone. When $R_1'$ and $R_7'$ are methyl, the compound is known as camphor. Norcamphor (and its methyl derivatives) are natural products. Compounds of the type wherein $R_1'$ and $R_3'$ are $C_2$–$C_5$ alkyl may be prepared by the base-catalyzed alkylation of norcamphor with the appropriate alkyl halide.

The tricyclodecane group (and its alkyl substituted derivatives) may be described as derivatives of octahydro-4,7-methano-indene, which may be represented by graphic formula VII.

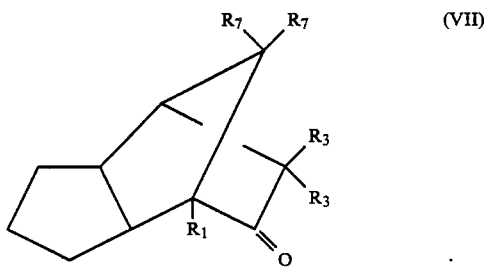

(VII)

Compounds represented by graphic formulae I–III may be prepared by reaction of the appropriate acetylenic alcohol derived from the ketone in formula VI with alpha- or beta- naphthol (or the appropriately substituted alpha- or beta- naphthol) or phenol (or the appropriately substituted phenol) in the presence of an acid catalyst, e.g., sulfuric acid, in a suitable solvent, e.g., toluene, at about 110° C. to 140° C.

The compounds represented by graphic formula IV may be prepared by in a manner similar to that described for the compounds of graphic formulae I–III but utilizing the octahydro-4,7-methanoindene-5-one of graphic formula VII.

Introduction of a norcamphor-type group at the 2-position of the naphthospiropyran ring gives rise to a system of two isomeric napthopyrans, each of which isomers gives rise to four isomeric colored forms - all of which have no elements of symmetry but which have similar colors. The lack of symmetry exhibited by such isomers results in a significant increase in their solubility in organic solvents and organic plastics compared to compounds that exhibit symmetrical elements. For example, the adamantane substituted spiropyrans described in EP Publication 246,114 (and their colored forms) possess a plane of symmetry parallel to and in the plane of the aromatic ring(s).

Compounds represented by graphic formulae I–IV may be used in photochromic applications, such as lenses for ophthalmic glasses, plano sun glasses, face shields, goggles, visors, camera lenses, windows, windshields, aircraft transparencies, plastic films and sheets, textiles and coatings, e.g., coating compositions such as paints. In general, benzospiropyrans represented by graphic formula I exhibit color changes from colorless to yellow-orange or red in unfiltered sunlight. Naphthospiropyrans represented by graphic formulae II, III and IV exhibit color changes from colorless to colors ranging from yellow to deep orange.

Of particular current interest are the following benzospiropyrans and naphthospiropyrans:

(1) Fenchane-2,2'-spiro[2H-2,1b]naphthopyran.
(2) Fenchane-2,2'-spiro[2H-1,2b]naphthopyran.
(3) Fenchane-2,2'-spiro[2H-1,2b]-6-phenyl naphthopyran.
(4) Camphane-2,2'-spiro[2H-2,1b]naphthopyran.
(5) Camphane-2,2'-spiro[2H-1,2b]naphthopyran.
(6) Norcamphane-2,2'-spiro[2H-2,1b]naphthopyran.
(7) Norcamphane-2,2'-spiro[2H-1,2b]naphthopyran.
(8) Octahydro-4'7'-methanoindene-5',2-spiro[2H,2,1b]naphthopyran.
(9) Octahydro-4'7'-methanoindene-5',2-spiro[2H,1,2b]naphthopyran.

The benzospiropyrans and naphthospiropyrans described herein may be dissolved in common organic solvents such as benzene, toluene, chloroform, ethyl acetate, methyl ethyl ketone, acetone, ethyl alcohol, methyl alcohol, acetonitrile, tetrahydrofuran, dioxane, methyl ether of ethylene glycol, dimethylformamide, dimethylsulfoxide, methyl Cellosolve, morpholine and ethylene glycol. They may also be dispersed in liquids containing water and/or alcohols.

The aforedescribed spiropyran compounds may also be dissolved in colorless or transparent solutions prepared from transparent organic host materials, e.g., transparent polymers (or copolymers) or blends of such transparent polymers and optionally a suitable organic solvent, e.g., polymers of transparent organic host materials described hereinafter dissolved in one or more of the aforedescribed organic solvents. Examples of such solutions include a poly(vinyl acetate)-acetone solution, a nitrocellulose-acetonitrile solution, a poly(vinyl chloride)-methyl ethyl ketone solution, a poly(methylmethacrylate)-acetone solution, a cellulose acetate-dimethylformamide solution, a poly(vinyl pyrrolidone)-acetonitrile solution, a polystyrene-benzene solution and an ethyl cellulose-methylene chloride solution. The aforesaid photochromic solutions or compositions may be applied to a compatible host material, e.g., a transparent support, such as cellulose triacetate, polyethylene terephthalate or baryta paper and dried to obtain an article that will color on exposure to ultraviolet radiation and that will return to its original state by removing the source of ultraviolet radiation.

The spiropyran compounds described herein (or compositions containing them) may be applied to or incorporated within a coating composition applied to a compatible support; or applied to or incorporated within the article comprising the compatible host, e.g., a polymerized organic material such as a synthetic polymeric plastic host material.

The benzospiropyrans and naphthospiropyrans described hereinabove are soluble in synthetic plastic materials customarily used for plastic optical lenses, both plano and ophthalmic, e.g., materials such as methyl methacrylate, polycarbonates and polymerizates prepared from CR⓪-39 diallyl glycol carbonate monomer. Of the spiropyran compounds depicted in graphic formulae 1–IV, the naphthopyran compounds, particularly the alpha-naphthopyran compounds, are currently preferred for use in preparing photoreactive optical lenses for the reason that such compounds exhibit photochromic properties to a marked degree and have a high solubility in synthetic plastic media compared to other described photochromic benzo- or naphthospiropyrans. Photochromic materials for photoreactive lenses preferably have the following stated desirable properties; namely, (a) a high quantum yield for coloring in the near ultraviolet, (b) a low quantum yield for bleaching with visible light, and (c) a fast thermal fade at ambient temperatures, but not so fast that the photochromic material does not color in unfiltered sunlight at ambient temperatures. In addition, the aforesaid properties are desirably retained in conventional rigid synthetic plastic materials customarily used for ophthalmic and plano lenses when such materials are treated to contain such spiropyran compounds.

On irradiation of the compounds of formula II-IV with ultraviolet light, the naphthospiropyran ring opens reversibly at the carbon-oxygen bond between the number 2-carbon atom and the ring oxygen to form two cis and two trans structures. The formation of the open forms of the two colorless compounds is believed to be responsible for the coloring observed on exposure to ultraviolet light.

The colored forms of the photochromic compounds of graphic formulae I-IV will fade to the colorless state at normal ambient temperatures when not exposed to ultraviolet light. Generally, the cisoid forms of the open or colored forms of the compound will fade more rapidly than the transoid forms. The face rate of the colored forms of the naphthospiropyran compounds of graphic formula II may be modified, for example, by introducing various substituent groups in the $R_5$ position of the molecule. Generally, the presence of bulky groups in this position will increase the fade rate.

For sunglass applications, norcamphor-2,2'spiro[2H-1,2b]-naphthopyrans, and derivatives thereof are deemed to be of particular interest. Derivatives of such naphthopyrans contemplated include the methyl-substituted derivatives, those derivatives in which a $C_1$-$C_5$ alkyl, e.g., methyl, is located at the 5-position ($R_5$), and those derivatives that are both substituted with a $C_1$-$C_5$ alkyl at the 5-position and substituted additionally on the naphthalene ring, e.g., at the 6- or 9-position by a $C_1$-$C_4$ alkyl, e.g., methyl, chlorine, bromine, $C_1$-$C_4$ alkoxy, e.g., methoxy, phenyl, or $C_1$-$C_4$ alkoxy phenyl, e.g. p-methoxyphenyl.

The compounds of the present invention may be prepared by a process based on a Claisen rearrangement. In such process, the benzospiropyran and naphthospiropyran compounds described herein are prepared by heating the appropriate phenol or naphthol with, for example, 2-ethynyl-2-hydroxy norcamphor in an organic solvent and in the presence of a suitable acid catalyst under mild reaction conditions for a time sufficient to complete the reaction, i.e., usually between about 2 and about 6 hours. Organic solvents that may be used include toluene and xylene. Reaction temperatures will vary and typically range from about 100° C. to about 160° C. The particular reaction temperature will be a function of the boiling point of the chosen solvent. For example, when xylene is used as the solvent, reaction temperatures will generally be about 140° C., whereas if toluene is used as the solvent, reaction temperatures will typically be about 110° C. Examples of suitable acid catalysts include sulfuric acid, polyphosphoric acid, acidic alumina, chloroacetic acid, toluene-p-sulfonic acid or other acid catalysts. The reaction for the benzospiropyran of graphic formula I wherein all R' substituents are hydrogen (norcamphor) may be expressed by the following equation:

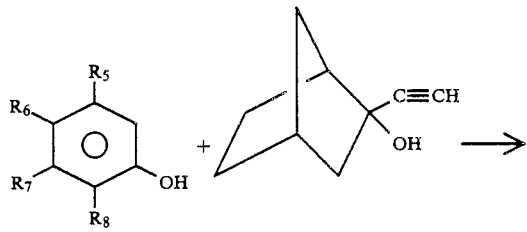

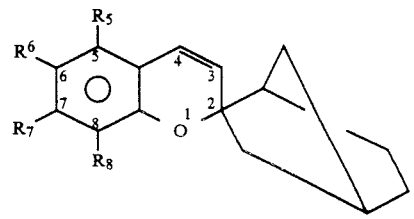

wherein $R_5$, $R_6$, $R_7$ and $R_8$ are the same as defined with respect to graphic formula I. In place of the phenol depicted in the above equation, a corresponding naphthol may be used to prepare naphthospiropyrans of graphic formulae II and III. The 2-ethynyl-2-hydroxy norcamphor reactant may be prepared by reacting norcamphor (or its alkyl homologues), e.g., camphor or fenchone, which are commercially available, with lithium acetylide, which is commercially available as an ethylene diamine complex, in a suitable organic solvent, such as tetrahydrofuran, dimethyl sulfoxide, xylene or toluene, in the presence of a small amount of acid catalyst, such as concentrated sulfuric acid. The 2-ethynyl-2-hydroxy norcamphor reactant may be obtained in high yields.

Commercially available photoreactive inorganic glass lenses containing silver halide particles darken to a gray or brown color in sunlight. In order to duplicate this color change in a plastic lens using the organic photochromic chromenes described in this application, it is contemplated that such compounds be used in combination with other appropriate complementary organic photochromic materials so that together they produce the desired gray or brown color shade when the plastic lens containing such photochromic materials are exposed to ultraviolet light. For example, a compound which colors to yellow may be blended with a compound that colors to an appropriate purple to produce a brown shade. Similarly, a compound which is orange in its colored state will produce a shade of gray in conjunction with an appropriate blue coloring compound.

Spiro(indolino) pyrido benzoxazine photochromic compounds described in U.S. Pat. No. 4,637,698 and spiro(indolino) naphthoxazines described in U.S. Pat. Nos. 3,562,172, 3,578,602, 4,215,010 and 4,342,668 are reported to color to purple or blue when activated, and these compounds may be used in admixture with or in conjunction with the yellow-orange photochromic compounds described in this application to obtain a near gray color when exposed to unfiltered sunlight.

The aforesaid spiro(indolino)-type compounds may be represented by the following graphic formula:

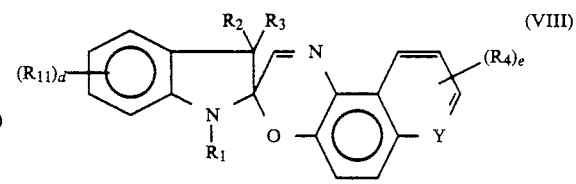

In the above graphic formula VIII, $R_1$ is selected from the group consisting of $C_1$-$C_8$ alkyl, e.g., methyl, ethyl, propyl, butyl, etc., phenyl, phen($C_1$-$C_4$)alkyl, e.g., benzyl, naphth($C_1$-$C_4$)alkyl, e.g., 1-naphthylmethyl, allyl, acrylyl($C_2$-$C_6$)alkyl, methacrylyl($C_2$-$C_6$)alkyl, carboxy($C_2$–$C_6$)alkyl, e.g., β-carboxyethyl, γ-carboxypropyl, δ-carboxybutyl, cyano ($C_2$–$C_6$)alkyl, e.g., β-cyanoethyl, γ-cyanopropyl, β-cyanoisopropyl, and δ-cyanobutyl, $C_1$–$C_4$ acyloxy($C_2$–$C_6$)alkyl, i.e., [$R_cC(O)OR_d$—, wherein $R_c$ is a $C_1$–$C_4$ alkyl and $R_d$ is a $C_2$–$C_6$ alkyl], e.g., acetoxyethyl, acetoxypropyl, propionyloxyethyl, acetoxybutyl, and propionyloxypropy, hydroxy($C_2$–$C_6$)alkyl, e.g., hydroxyethyl, hydroxypropyl and hydroxybutyl, $(C_2H_4O)_m$·$CH_3$, wherein m is a number of from 1 to 6, and mono- and disubstituted phenyl, said phenyl substituents being selected from $C_1$–$C_4$ alkyl and $C_1$–$C_5$ alkoxy, e.g., methoxy ethoxy, propoxy, butoxy and pentoxy. Preferably, $R_1$ is selected from the group consisting of $C_1$–$C_4$ alkyl, phenyl, benzyl, 1-naphth($C_1$–$C_2$)alkyl, such as 1-naphthylmethyl, carboxy($C_2$–$C_4$)alkyl, cyano($C_2$–$C_4$)alkyl, $C_1$–$C_4$ acyloxy($C_2$–$C_4$)alkyl, e.g., $C_1$–$C_4$ acyloxyethyl, hydroxy($C_2$–$C_4$)alkyl, e.g., $(C_2H_4O)_m$·$CH_3$, wherein m is a number of from 1 to 3, e.g., 2.

$R_2$ and $R_3$ of the above graphic formula VIII are each selected from the group consisting of $C_1$–$C_5$ alkyl, phenyl, mono- and disubstituted phenyl, benzyl, or $R_2$ and $R_3$ may combine to form a cyclic ring selected from the group consisting of an alicyclic ring containing from 6 to 8 carbon atoms (including the spiro carbon atom), norbornyl and adamantyl. The aforesaid phenyl substituents may be selected from $C_1$–$C_4$ alkyl and $C_1$–$C_5$ alkoxy radicals. More particularly, $R_2$ and $R_3$ are each selected from $C_1$–$C_5$ alkyl, e.g., methyl, ethyl, propyl, butyl and pentyl, phenyl. When one of $R_2$ or $R_3$ is a tertiary alkyl radical, such as tertiary butyl or tertiary amyl, the other is preferably an alkyl radical other than a tertiary alkyl radical.

Y in graphic formula VIII may be carbon or nitrogen. The number and type of non-hydrogen substituent groups represented by $R_4$ will vary depending upon whether Y is carbon or nitrogen. Generally, when Y is carbon each $R_4$ substituent may be selected from the group consisting of halogen, e.g., chloro, fluoro, or bromo, $C_1$–$C_5$ alkyl, $C_1$–$C_5$ alkoxy, e.g., methoxy, ethoxy, propoxy, butoxy and pentoxy, nitro, cyano, thiocyano, $C_1$–$C_4$ monohaloalkyl, e.g., $C_1$–$C_4$ monochloroalkyl, such as chloromethyl and chloroethyl, $C_1$–$C_2$polyhaloalkyl, as, for example, triahloalkyl such as trichloroalkyl or trifluoroalkyl, e.g., trifluoromethyl and 2,2,2-trifluoroethyl, and monoalkylamino or dialkylamino wherein the alkyl moiety of the alkylamino group contains between one to four carbon atoms, e.g., methylamino, ethylamino, propylamino, dimethylamino and diethylamino.

The letter "e" in graphic formula VIII is a number of from 0 to 1 or 2, e.g., 1, and denotes the number of non-hydrogen substituents. In particular, when "e" is 1 or 2 and Y is carbon, each $R_4$ substituent may be selected from the group $C_1$–$C_2$ alkyl, $C_1$–$C_2$ alkoxy, chloro, fluoro, bromo, nitro, and trifluoromethyl. When "e" is 0 (zero), there are no non-hydrogen substituents and all of the aromatic carbon atoms have their full complement of hydrogen atoms.

When Y is nitrogen, each $R_4$ non-hydrogen substituent may be selected from $C_1$–$C_5$ alkyl, e.g., $C_1$–$C_2$ alkyl, $C_1$–$C_5$ alkoxy, e.g., $C_1$–$C_2$ alkoxy, and halogen, e.g., chloro, fluoro or bromo. Typically, "e" is 0 (zero) when Y is nitrogen and thus there are no non-hydrogen substituents.

$R_{11}$ in graphic formula VIII may be selected from $C_1$–$C_5$ alkyl, halogen, $C_1$–$c_5$ alkoxy, nitro, cyano, $C_1$–$C_4$ monohaloalkyl, $C_1$–$C_4$ polyhaloalkyl, $C_1$–$C_8$ alkoxycarbonyl, $C_1$–$C_4$ acyloxy, i.e., $R_cC(O)O$—, wherein $R_c$ is a $C_1$–$C_4$ alkyl, e.g., methyl. The letter "d" in graphic formula VIII may vary from 0 to 4, e.g., 0 to 2, such as 1 or 2, and denotes the number of non-hydrogen substituents. When "d" is 0 (zero), there are no non-hydrogen substituents as described with respect to "e".

More particularly, the spiro(indolino) pyridobenzoxazines may be represented by the following graphic formula:

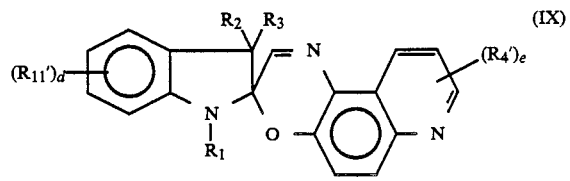

In graphic formula IX, $R_1$, $R_2$ and $R_3$ are the same as defined with respect to graphic formula VIII. $R_4'$ may be selected from $C_1$–$C_5$ alkyl, e.g., $C_1$–$C_2$ alkyl, $C_1$–$C_5$ alkoxy, e.g., $C_1$–$C_2$alkoxy and halogen, e.g., chloro, fluoro or bromo. The letter "e" may vary from 0 to 1. Commonly, "e" is 0, and thus, there are no non-hydrogen substituents. When "e" is 1, the $R_4'$ substituent may be located on any of the available carbon atoms of the pyridobenz moiety of the pridobenzoxazine portion of the compound, i.e., at the 5', 6', 8' 9' or 10' positions, most usually at the 8', 9' or 10' positions. When "e" is 2, the $R_4'$ substituent may be the same or different and, in either case, are selected from the above-described group and are located at two of the aforedescribed available carbon atoms.

$R_{11}'$ in graphic formula IX may be selected from the group consisting of $C_1$–$C_5$ alkyl, e.g., methyl, ethyl, propyl, butyl and pentyl, halogen, e.g., chloro and fluoro, $C_1$–$C_5$ alkoxy, e.g., methoxy, ethoxy, propoxy, butoxy and pentoxy, nitro, cyano, $C_1$–$C_4$ monohaloalkyl, e.g., chloromethyl, fluoromethyl, chloroethyl, chloropropyl, etc., $C_1$–$C_4$ polyhaloalkyl, e.g., trihaloalkyl, $C_1$–$C_8$ alkoxycarbonyl, and $C_1$–$C_4$ acyloxy, i.e., $R_cC(O)O$—, wherein $R_c$ is a $C_1$–$C_4$ alkyl, e.g., methyl. An example of an acyloxy group is acetoxy. While any halogen, i.e., chlorine, bromine, iodine and fluorine say be used in respect to the aforesaid halogen or haloalkyl substituents, chlorine, fluorine and bromine, particularly chlorine and fluorine, are preferred for the halogen substituent and fluorine is preferred for the polyhaloalkyl substituent, e.g., trifluoromethyl, ($CF_3$). Preferably, $R_{11}'$ is selected from the group consisting of $C_1$–$C_2$ alkyl, chlorine, fluorine, $C_1$–$C_2$ trihaloalkyl, e.g., trihalomethyl such as trifluoromethyl and $C_1$–$C_5$ alkoxy.

The letter "d" in graphic formula IX is a number from 0 to 4, e.g., 0 to 2, such as 1 or 2. When "d" is 2 or more, the $R_{11}$ substituent may be the same or different and in either case, are selected from the aforedescribed group. The $R_{11}'$ substituent(s) may be located on any of the available carbon atoms of the indolino portion of the compound, i.e., . at the 4, 5, 6 or 7 positions. When "d" is 2, the $R_{11}'$ substituents may be present at the 4 and 5, 5 and 6, 4 and 7 or 6 and 7 carbon atoms of the indolino moiety.

It is possible that the photochromic organic substances of graphic formula IX (and X) may be a mixture of isomers due to the alternative directional mechanism by which intramolecular condensation occurs during formation of the starting indole reactant (Fischer's base). Indolization of 3-substituted phenylhydrazones can give rise to a 4-substituted indole, a 6-substituted indole, or mixtures thereof. Thus, when "d" is 1, the photochromic substances may be substituted at the 4 position on the indoline ring, at the 6 position of that ring or comprise a mixture of such isomers. When "d" is 2, the photochromic substance may be substituted at any combination of the 4, 5, 6, or 7 carbon atoms of the indoline ring (as heretofore indicated) and may comprise an isomeric mixture of such compounds, e.g., a mixture of compounds having substituents at the 4 and 5, 4 and 6, 5 and 6, 4 and 7, 5 and 7, and 6 7 positions of the indoline ring. Commonly, when "d" is 2 the substituents are located at the 4 and 5, or 5 and 6 positions. Also contemplated are materials containing mixtures of such isomers, e.g., materials comprising 4 (and 6) and 5-substituted spiro(indolino benzoxazines.

Examples of spiro(indolino) pyridobenzoxazines selected from the description of graphic formula IX that may be employed in the process of the present invention are described in Table 1. Such pyridobenzoxazines are those in which $R_1$, $R_2$, $R_3$, and $R_{11}'$ are as indicated in Table 1, the letter "e" is 0 (zero). and the letter "d" is 0, 1 or 2. A hyphen (—) indicates the absence of a non-hydrogen substituent.

TABLE 1

| Compound/ | $R_1$ | $R_2$ | $R_3$ | $R_{11}'$ | $R_{11}'$ |
|---|---|---|---|---|---|
| 1 | $CH_3$ | $CH_3$ | $CH_3$ | — | — |
| 2 | $CH_3$ | $CH_3$ | $CH_3$ | 4-$CH_3$ | 5-$CH_3$ |
| 3 | $CH_3$ | $CH_3$ | $CH_3$ | 5-$OCH_3$ | — |
| 4 | $CH_3$ | $CH_3$ | $CH_3$ | 5-Cl | 6-$CH_3$ |
| 5 | $CH_3$ | $CH_3$ | $C_2H_5$ | — | — |
| 6 | $CH_3$ | $CH_3$ | $C_2H_5$ | 5-$CH_3$ | 6-$CH_3$ |
| 7 | $CH_3$ | $C_2H_5$ | $C_2H_5$ | — | — |
| 8 | n-$C_4H_9$ | $CH_3$ | $C_2H_5$ | — | — |
| 9 | $CH_3$ | $CH_3$ | phenyl | — | — |
| 10 | $CH_3$ | phenyl | phenyl | — | — |
| 11 | $C_2H_5$ | $CH_3$ | $C_2H_5$ | 4-$CH_3$ | 5-$CH_3$ |
| 12 | n-$C_4H_9$ | $CH_3$ | $C_2H_5$ | 5-$CH_3$ | 6-$CH_3$ |
| 13 | $CH_3$ | $CH_3$ | $CH_3$ | 5-$CH_3$ | 6-$CH_3$ |
| 14 | n-$C_3H_7$ | $CH_3$ | $CH_3$ | 5-$OCH_3$ | — |

Compound 2 in Table 1 may be named 1,3,3,4,5-pentamethylspiro[indolino-2,3' [3H]pyrido [3,2-f][1,4] benzoxazine]. Similarly, compound 6 in Table 1 may be named 1,3,5,6-tetramethyl-3-ethylspiro[indoino-2,3' [3H]pyrido [2,3-f][1,4]benzoxazine]. Other compounds in Table 1 may be similarly named taking into account the different substituents. Moreover, compounds selected from the description of graphic formula IX may be similarly named by substituting the substituents described with respect to $R_1$, $R_2$, $R_3$, $R_4$ and $R_{11}'$ for those found in Table 1. When the letter "e" is 1 or more, the $R_4'$ substituent(s) are given a prime (') designation. Numbering of the pyrido benzoxazine portion of the molecule is counter clockwise starting with the nitrogen atoms of the oxazine ring as the 1' position.

Spiro(indolino)naphthoxazines that may be used in the practice of the present process may be represented by the following graphic formula:

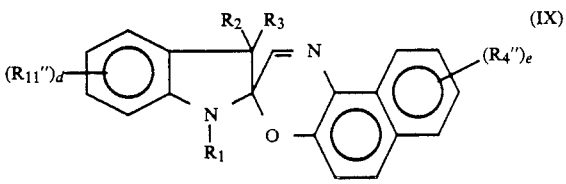

wherein $R_1$, $R_2$ and $R_3$ are the same as that described with respect to graphic formula I.

$R_4''$ in graphic formula X may be selected from the group consisting of halogen, e.g., chloro, fluoro, or bromo, $C_1$-$C_5$ alkyl, $C_1$-$C_5$ alkoxy (e.g., methoxy, ethoxy, propoxy, butoxy and pentoxy), nitro, cyano, thiocyano, $C_1$-$C_4$ monohaloalkyl, e.g., $C_1$-$C_4$ monochloroalkyl, such as chloromethyl and chloroethyl, $C_1$-$C_2$ polyhaloalkyl, as for example, trihaloalkyl, such as trichloroalkyl or trifluoroalkyl, e.g., trifluoromethyl and 2,2,2-trifluoroethyl, and monoalkylamino or dialkylamino, wherein the alkyl moiety of the alkylamino group contains from 1 to 4 carbon atoms, e.g., methylamino, ethylamino, propylamino, dimethylamino and diethylamino. More particularly, the $R_4$ substituent may be selected from the group $C_1$-$C_2$ alkyl, $C_1$-$C_2$ alkoxy, chloro, fluoro, bromo, nitro and trifluormethyl, The letter "e" in graphic formula X is a number from 0 to 2, e g., 1 or 2, and denotes the number of non-hydrogen substituents. When "e" is 0, all of the substituents on the available carbon atoms of the naphtho moiety of the molecule represented by formula X are hydrogen.

As in the case with graphic formula IX, when "e" is 1, the $R_4'$ substituent may be located on any of the available carbon atoms of the naphtho moiety of the naphthoxazine portion of the molecule, i.e., at the 5', 6', 7' 8', 9' or 10' positions. Preferably, the $R_4''$ substituent is present on the 7', 8' or 9' carbon atoms. When "e" is 2, the $R_4''$ substituents may be same or different and in either case are selected from the above described group. When "e" is 2, the $R_4''$ substituents are commonly located at the 7' and 9', or 8' and 10' positions. Numbering of the naphthoxazine portion of the molecule is done in the same manner as that described with regard to the pyrido benzoxazine portion of the molecule of formula IX. $R_{11}''$ and the letter "d" in graphic formula X are the same as that described with respect to graphic formula VIII.

Non-limiting examples of spiro(indolino) naphthoxazines selected from the description of graphic formula X that may be used in the practice of the present invention are described in Table 2. Such spiro(indolino) naphthoxazines are those in which $R_1$, $R_2$, $R_3$, $R_4''$ and $R_{11}''$ are as indicated in Table 2, the letter "d" is 0, 1 or 2 and the letter "e" is 1. As in Table 1, a hyphen (-) indicates the absence of a non-hydrogen substituent. In Table 2, all of the $R_4''$ substituents are at the 9'-position.

| Compound/ | $R_1$ | $R_2$ | $R_3$ | $R_4''$ (9'-) | $R_{11}''$ | $R_{11}''$ |
|---|---|---|---|---|---|---|
| 1 | $CH_3$ | $CH_3$ | $CH_3$ | $OCH_3$ | — | — |
| 2 | $CH_3$ | $CH_3$ | $CH_3$ | $OCH_3$ | 4-$CH_3$ | 6-$CH_3$ |
| 3 | $CH_3$ | $CH_3$ | $CH_3$ | $OCH_3$ | 5-$OCH_3$ | — |
| 4 | $CH_3$ | $CH_3$ | $CH_3$ | $OCH_3$ | 5-Cl | 6-$CH_3$ |
| 5 | $CH_3$ | $CH_3$ | $C_2H_5$ | $OCH_3$ | — | — |
| 6 | $CH_3$ | $CH_3$ | $C_2H_5$ | $OCH_3$ | 5-$CH_3$ | 6-$CH_3$ |

-continued

| Compound/ | $R_1$ | $R_2$ | $R_3$ | $R_4''$ (9'-) | $R_{11}''$ | $R_{11}''$ |
|---|---|---|---|---|---|---|
| 7 | $CH_3$ | $C_2H_5$ | $C_2H_5$ | $OCH_3$ | — | — |
| 8 | $n-C_4H_9$ | $CH_3$ | $C_2H_5$ | $OCH_3$ | — | — |
| 9 | $CH_3$ | $CH_3$ | phenyl | $OCH_3$ | — | — |
| 10 | $CH_3$ | phenyl | phenyl | $OCH_3$ | — | — |
| 11 | $CH_3$ | $p-C_6H_4OCH_3$ | $p-C_6H_4OCH_3$ | $OCH_3$ | — | — |
| 12 | $C_2H_5$ | $CH_3$ | $C_2H_5$ | $OCH_3$ | $5-CH_3$ | — |
| 13 | $n-C_4H_9$ | $CH_3$ | $C_2H_5$ | $OCH_3$ | $5-CH_3$ | — |

Compound 2 in Table 2 may be named 1,3,3,5,6-pentamethyl-9'methoxy-spiro [indolino-2,3' [3H]-naphth [2,1-b][1,4]-oxazine]. Similarly, compound 6 in Table 2 may be named 1,3,5,6-tetramethyl-3-ethyl-9'-methoxyspiro [indolino-2,3' [3H]-naphth [2,1-b] . [1,4]-oxazine. Other compounds in Table 2 can be similarly named taking into account the different substituents. Moreover, compounds selected from the description of graphic formula X may be similarly named.

The benzospiropyran or naphthospiropyran compounds of the present invention may be combined with spiro(indolino) pyrido benzoxazine or spiro(indolino) naphthoxazine compounds in amounts and in a ratio such that an organic host material to which the mixture of compounds is applied or in which they are incorporated exhibits a substantially neutral color when activated with unfiltered sunlight, i.e., as near a neutral color as possible given the colors of the activated pyran and oxazine photochromic compounds. The relative amounts of the oxazine and pyran compounds used will vary and depend in part upon the relative intensities of the color of the activated species of such compounds. Generally, the mole ratio of the spiro (indolino) oxazine compound to the pyran compound will vary from about 1:3 to about 3:1, e.g., between about 1:2 and about 2:1.

Photochromic compounds of the present invention, mixtures of such compounds with other photochromic compounds, or compositions containing same (hereinafter "photochromic substances") may be applied to or incorporated into a host material by various methods described in the art. Such methods include dissolving or dispersing the substance within the host material, e.g., imbibition of the photochromic substance into the host material by immersion of the host material in a hot solution of the photochromic substance or by thermal transfer; providing the photochromic substance as a separate layer between adjacent layers of the host material, e.g., as a part of a polymer film; and applying the photochromic substance as part of a coating placed on the surface of the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms. For example:

(a) The photochromic substance may be mixed with a polymerizable composition that, upon curing, produces a polymeric host material and the polymerizable composition cast as a film, sheet or lens, injection molded or otherwise formed into a sheet or lens, or polymerized by emulsion or suspension polymerization to form a photochromic particulate material that may be used as a pigment;

(b) The photochromic substance may be dissolved or dispersed in water, alcohol or other solvents or solvent mixtures and then imbibed into the solid host material by immersion of the solid host material for from several minutes to several hours, e.g., 2–3 minutes to 2–4 hours, in a bath of such solution or dispersion. The bath is conventionally at an elevated temperature, usually in the range of 50°–120° C.; however, higher temperatures may be used. Thereafter, the host material is removed from the bath and dried;

(c) The photochromic substance may also be applied to the surface of the host material by any convenient manner, such as spraying, brushing, spin-coating or dip-coating from a solution or dispersion of the photochromic substance in the presence of a polymeric binder. Thereafter, the photochromic substance is imbibed into the host material by heating it, e.g, in an oven, for from a minute to several hours, e.g., 2 to 3 hours, at temperatures in the range of from 80°–180° C., e.g., 100°–150° C.;

(d) In a variation of the preceding imbibition procedure, the photochromic substance may be deposited onto or absorbed by a temporary support, e.g., a sheet of kraft paper, aluminum foil, polymer film or fabric, which is then placed in near proximity to or in contact with the host material and heated, e.g., in an oven. This and the preceding procedure may be repeated one or more times to imbibe the desired amount of photochromic substance into the host material;

(e) The photochromic substance may be dissolved or dispersed in a transparent polymeric material which may be applied to the surface of the host in the form of an adherent film by any suitable technique such as spraying, brushing, spin-coating or dip-coating; and finally (f) The photochromic substance may be incorporated in or applied to a transparent polymeric material by any of the above-mentioned methods, which can then be placed within the host material as a discrete layer intermediate to adjacent layers of the host material(s).

In addition, imbibition of photochromic substances into a host material may be accomplished by the method described in U.K. Patent Application 2,174,711, which is hereby incorporated in toto by reference. In that method a substantially mottle-free, substantially homogeneous film of polymeric resin having the photochromic substance dissolved therein is applied to the surface of the host material. The film-bearing host material is heated to temperatures near to but below the melting temperature of the Photochronic substance for a time sufficient to incorporate a photochromic amount of the photochromic substance into the surface of the host. The photochromic-depleted film is then removed from the host surface with a suitable solvent.

Imbibition of photochromic substances into a host material, e.g., an ophthalmic lens, may be performed readily also by dissolving the photochromic substance in a suitable solvent, e.g., toluene, and absorbing the resulting solution into a temporary substrate, such as filter paper or other substrates described in subparagraph (d) above. The concentration of the photochromic substance in the solvent may vary and will depend on the solubility of the substance in the solvent used. Suitably, the photochromic substance will be present in the solvent at a concentration of from about 5 to 15, e.g., 10, weight percent. The temporary substrate may be a flexible material that can take the shape of the surface of the host material on which it is placed if such surface is irregular or not flat, such as the curved surface of the lens.

The temporary substrate containing the solution of photochromic substances is dried to remove the solvent and the substrate placed in contact with the surface of the host material. Optionally, a metal cap having the shape of the host material surface is placed on top of the temporary substrate to insure uniform contact of the interface of the substrate and host surface. For example, when the host is a lens, the cap and temporary substrate should be shaped to conform to the shape of the lens, e.g., the convex or concave surface of the lens. This sandwich comprising the metal cap-temporary substrate-host material is then heated for a time sufficient to imbibe a photochromic amount of the photochromic substance(s) into the subsurface of the host material. Heating times may range from about 15 minutes to 180 minutes, usually from 45 to 120 minutes at transfer temperatures, which may range from 125° C. to 155° C.

The aforesaid process may be repeated one or more times, e.g., two or three times, to imbibe the desired amount of photochromic substance into the subsurface of the host material, e.g., to a depth beneath the surface of up to about 50 microns. In the case of semi-finished lenses, the imbibition process is performed on the front (convex) surface of the lens to allow finishing (grinding) of the back (concave) surface. Further, the edges of the lens may be ground to remove imperfections before thermally transferring the photochromic substances. If desired, the host material may then be tinted with a color compatible dye e.g., a brown, yellow-brown or gray dye.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

Typically, tinting is accomplished by immersion of the host material in a heated aqueous dispersion of the selected dye. The degree of tint is controlled by the temperature of the dye bath and the length of time the host material is allowed to remain in the bath. Generally, the dye bath is at temperatures of less than 100° C., e.g., from 70° C. to 90° C., such as 80° C., and the host material remains in the bath for less than five (5) minutes, e.g., between about 0.5 and 3 minutes, e.g., about 2 minutes. The degree of tint is such that the resulting article exhibits from about 70 to 85 percent, e.g., 80–82 percent, light transmission.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers, e.g., a polyvinyl alcohol coating. Such coatings are known in the art.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should rot be such that it masks the color of the activated form of the photochromic substance, i.e., so the change in color is readily apparent to the observer. Preferably, the host material article is a solid transparent material or an optically clear material, e.g., materials suitable for ophthalmic elements, such as ophthalmic lenses, or materials useful for applications such as windows, windshields, aircraft transparencies, etc.

Examples of host materials which may be used with the photochromic substances or compositions described herein include: polymers, i.e., homopolymers and copolymers, of polyol(allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate) copoly(styrene-acrylonitrile), polyvinylbutyral and polymers, i.e., homocopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of the transparent polymers are also suitable as host materials. Preferably, the host material is an optically clear polymerized organic material prepared from a polycarbonate resin, such as the carbonate-linked resin derived from bisphenol A and phosgene, which is sold under the trademark, LEXAN; a poly(methyl methacrylate), such as the material sold under the trademark, PLEXIGLAS; polymerizates of a polyol(allyl carbonate), especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of rom 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethan having terminal diacrylate functionality, as described in U.S. Pat. No. 4,360,653; cellulose acetate, cellulose propionate, cellulose butyrate, cellulose acetate butyrate, and polystyrene and copolymers of styrene with methyl methacrylate, vinyl acetate and acrylonitrile.

Polyol (allyl carbonate) monomers which may be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g, glycols. The monomers can be prepared by procedures well known in the art, e.g., J.S. Pat. No. 2,370,567 and 2,403,113.

The aforedescribed polyol (allyl carbonate) monomers may be represented by the graphic formula:

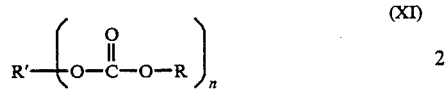

(XI)

wherein R is the radical derived from an unsaturated alcohol and is commonly an allyl or substituted allyl group, R' is the radical derived from the polyol, and n is a whole number from 2–5, preferably 2. The allyl group (R) may be substituted at the 2 position with a halogen, most notably chlorine or bromine, or an alkyl group containing from 1 to 4 carbon atoms, generally a methyl or ethyl group. The R group may be represented by the graphic formula:

(XII)

wherein $R_o$ is hydrogen, halogen, or a $C_1$–$C_4$ alkyl group. Specific examples of R include the groups: allyl, 2chloroallyl, 2bromoallyl, 2fluoroallyl, 2methylallyl, 2ethylallyl, 2isopropylallyl, 2-n-propylallyl, and 2-n-butylallyl. Most commonly R is the allyl group, $H_2C=CH-CH_2-$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$–$C_4$) alkylene glycol, i.e., ethylene glycol, propylene glycol, trimethylene glycol, tetramethylene glycol, or diethylene glycol, triethylene glycol, etc.

The aromatic polyol can be represented by the graphic formula:

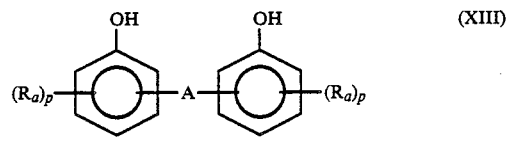

(XIII)

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene (isopropylidene), $R_a$ represents lower alkyl substituents of from 1 to 3 carbon atoms and halogen, e.g., chlorine and bromine, and p is 0, 1, 2, or 3. Preferably, the hydroxyl group is in the ortho or para position.

Specific examples of the radical R' include: alkylene groups containing from 2 to 10 carbon atoms such as ethylene, ($-CH_2-CH_2-$), trimethylene, methylethylene, tetramethylene, ethylethylene, pentamethylene, hexamethylene, 2-methylhexamethylene, octamethylene, and decamethylene; alkylene ether groups such as $-CH_2-O-CH_2-$, $-CH_2CH_2-O-CH_2CH_2-$, $-CH_2-O-CH-CH_2-$, and $-CH_2CH_2-O-CH_2CH_2CH_2-$; alkylene polyether groups such as $-CH_2CH_2-O-CH_2CH_2-O-CH_2CH_2-$, and $-CH_2CH_2CH_2-O-CH_2CH_2CH_2-O-CH_2CH_2CH_2-$; alkylene carbonate and alkylene ether carbonate groups such as $-CH_2CH_2-O-CO-O-CH_2CH_2-$ and $-CH_2CH_2-O-CH_2CH_2-O-CO-O-CH_2CH_2-O-CH_2CH_2-$; and isopropylidene is(para-phenyl),

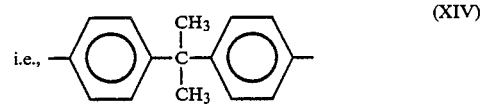

(XIV)

Most commonly, R' is $-CH_2CH_2-$, $-CH_2CH_2-O-CH_2CH_2-$, or $-CH_2CH_2-O-CH_2CH_2-O-CH_2CH_2-$.

Specific non-limiting examples of polyol (allyl carbonate) monomers include ethylene glycol bis(2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylens glycol bis(2ethylallyl carbonate), pentamethylene glycol bis(allyl carbonate), and isopropylidene bisphenol bis(allyl carbonate).

Industrially important polyol bis(allyl carbonate) monomers which may be utilized in the invention herein contemplated are:

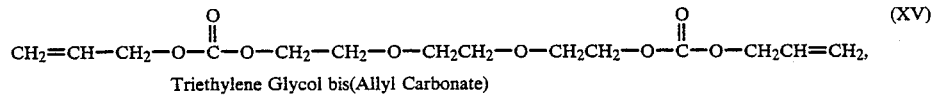

Triethylene Glycol bis(Allyl Carbonate)

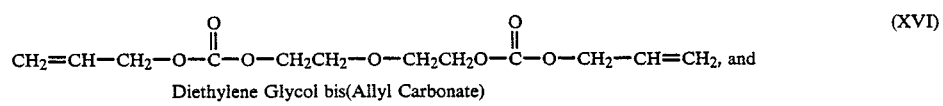

Diethylene Glycol bis(Allyl Carbonate)

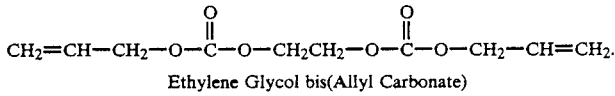

Ethylene Glycol bis(Allyl Carbonate)

Diethylene glycol bis(allyl carbonate) is preferred.

Because of the process by which the polyol(allyl carbonate) monomer is prepared, i.e., by phosgenation of the polyol (or allyl alcohol) and subsequent esterification by the allyl alcohol (or polyol), the monomer product can contain related monomer species in which the moiety connecting the allyl carbonate groups contains one or more carbonate groups. These related monomer species can be represented by the graphic formula:

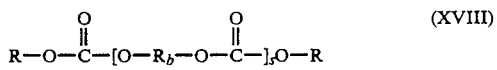

wherein R is as defined above, $R_b$ is a bivalent radical, e.g., alkylene or phenylene, derived from a diol, and s is a whole number from 2 to 5. The related monomer species of diethylene glycol bis(allyl carbonate) can be represented by the graphic formula,

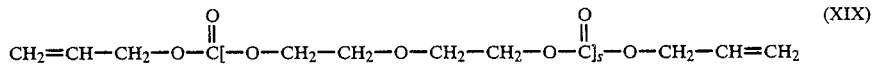

wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4 etc.

In addition, a partially polymerized form of the polyol (allyl carbonate) monomer, i.e., prepolymer, can be used. In that embodiment, the monomer is thickened by heating or partially polymerized by using small, e.g., 0.5–1.5 parts of initiator per hundred parts of monomer (phm), to provide a non-gel containing, more viscous monomeric material.

As used in the present description and claims, the term polyol(allyl carbonate) monomer or like names, e.g., diethylene glycol bis(allyl carbonate), are intended to mean and include the named monomer or prepolymer and any related monomer species contained therein.

Polyfunctional acrylate monomers that may be used to prepare synthetic polymeric host materials are esterification products of an acrylic acid moiety selected from the group consisting of acrylic acid and methacrylic acid, and a polyol, e.g., a diol, a triol or tetracarbinol. More particularly, the polyfunctional acrylate monomer may be represented by the following graphic formula:

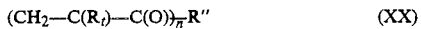

wherein $R_t$ is hydrogen or methyl, n is the number 2, 3, or 4, and R" is the multivalent radical, i.e., a bivalent, trivalent or quadravalent radical, remaining after removal of the hydroxy groups from a polyol, having from 2 to 4 hydroxy groups, e.g., a diol, a triol or tetracarbinol respectively. More particularly, $R_t$ is hydrogen or methyl, and n is 2 or 3, more usually 2.

R" may be selected from the group consisting of alpha, omega $C_2$–$C_8$ glycols, cyclohexane diol, diethylene glycol, triethylene glycol, tetraethylene glycol, dipropylene glycol, $C_2$–$C_5$ triols and pentaerythritol. Examples of such polyols include ethylene glycol, trimethylene glycol, 1,4-butane diol, 1,5-pentane diol, 1,6-hexane diol, propylene glycol, trimethylol propane, glycerol and the like.

Examples of polyfunctional acrylate monomers, such as diacrylates and triacrylates, include: ethylene glycol diacrylate, ethylene glycol dimethacrylate, 1,2-propane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-dimethyl-1,6-hexane diol dimethacrylate, diethylene glycol diacrylate, diethylene glycol dimethacrylate, triethylene glycol dimethyacrylate, trimethylol propane trimethacrylate, tetraethylene glycol diacrylate, tetraethylene glycol dimethacrylate, dipropylene glycol diacrylate, dipropylene glycol dimethacrylate, trimethylol propane triacrylate, glycerol triacrylate, glycerol trimethacrylate, pentaerythritol triacrylate, pentaerythritol dimethacrylate, pentaerythritol tetraacrylate, pentaerythritol tetramethacrylate and mixtures of such acrylate monomers.

A portion of the polyfunctional acrylate monomer may be replaced with a monofunctional copolymerizable monomer containing the vinyl ($CH_2=CH—$) grouping. Such compatible monomers include monofunctional acrylic and methacrylic acid esters, and vinyl esters of $C_2$–$C_6$ carboxylic acids, i.e., vinyl carboxylates. Preferably, the copolymerizable monomer is a non-aromatic, e.g., non-benzenoid, containing monomer. Monofunctional acrylic or methacrylic ester monomers may be graphically illustrated by the following formula,

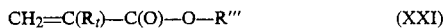

wherein $R_t$ is hydrogen or methyl, and R''' is selected from the group consisting of $C_1$–$C_{12}$, e.g., $C_1$–$C_8$, alkyl, $C_5$–$C_6$ cycloalkyl, glycidyl and hydroxyethyl. Preferably, R''' is a a $C_1$–$C_4$ alkyl, e.g., methyl or cyclohexyl.

Examples of monofunctional acrylic acid type monomers include, for example, the acrylic and methacrylic acid esters of alkanols such as methanol, ethanol, propanol, butanol, pentanol, hexanol, heptanol and octanol, e.g., methyl acrylate, methyl methacrylate, ethyl acrylate and ethyl methacrylate, cycloalkanols such as cyclopentanol and cyclohexanol, glycidol (3-hydroxy propylene oxide, (d, 1, dl)) and ethylene glycol. Examples of vinyl carboxylates include vinyl acetate, vinyl propionate, vinyl butyrate and vinyl valerate. In addition to and/or in place of the aforedescribed monofunctional copolyserizable monomer, monofunctional allylic and difunctional allylic copolymerizable compatible monomers may also replace a portion of the polyfunctional acrylate monomer. Monofunctional allylic monomers contemplated include allyl esters of $C_2$–$C_6$ carboxylic acids, $C_1$–$C_6$ allyl ethers and other copolymerizable allyl compounds. Preferably the monofunctional allylic monomer is a non-aromatic compound. Difunctional allylic copolymerizable monomers contemplated herein are the polyol (allyl carbonates) monomers of graphic formula XI.

The amount of photochromic substance or composition-containing same applied to or incorporated into a host material is not critical provided that a sufficient amount is used to produce a photochromic effect discernible to the naked eye. Generally such amount can be described as a photochromic amount. The amount used depends often upon the intensity of color desired upon irradiation thereof and upon the method used to incorporate or apply the photochromic substances. Typically, the more compound applied or incorporated, the greater is the color intensity. Generally, the amount of each photochromic substance incorporated into or applied to the host material ranges from about 0.01 to about 10 to 20 percent by weight. More typically, the amount of photochromic substance(s) incorporated into or applied to the host material will range from about 0.01 to about 2 weight percent, more particularly, from about 0.01 to about 1 weight percent, e.g., from about 0.1 or 0.5 to about 1 weight percent, based on the weight of the host material. Stated another way, the amount of each photochromic substance used to impart a photochromic effect will typically vary from about 0.1 to about 10, e.g., 0.5 to 2 milligrams of the photochromic substance per square inch of the surface of the host material independent of the thickness of the host material article.

The present invention is more particularly described in the following examples which are intended as illustrative only, since numerous modifications and variations therein will be apparent to those skilled in the art.

EXAMPLE 1

Lithium acetylide/ethylene diamine complex (5 grams, 54mmole) was added in small portions over 30 minutes to a solution of fenchone (8.2 grams, 54 mmole) in 50 cubic centimeters (cc) of dimethyl sulfoxide at room temperature. The reaction mixture was stirred at room temperature for three hours and then poured onto about 500 grams of crushed ice. The cooled reaction mixture was acidified with dilute (10 percent) hydrochloric acid and the organic reaction product extracted with diethyl ether (2×100 cc). The ether extract was dried over anhydrous magnesium sulfate, filtered, and the ether solvent evaporated from the filtrate leaving as an oil, 2-ethynyl-2-fenchol in near quantitative yield.

The alcohol, 2-ethynyl-2-fenchol (17.8 grams, 0.1 mole), and 2-naphthol (14.4 grams, 0.1 mole) were dissolved in xylene (70 cc). One drop of concentrated sulfuric acid was added to the xylene solution, which was boiled under reflux for three hours. The reaction solution was cooled and then washed sequentially with dilute (10 percent) sodium hydroxide and water. The organic layer was separated, diluted with diethyl ether (100 cc), dried over anhydrous magnesium sulfate and filtered. Ether solvent was removed and the residual oil was chromatographed on silica gel using petroleum (b.p. 60°–80° C.) as eluant. The photochromic fraction in the eluate was collected and the solvent removed by distillation. On standing, the residual colorless oil crystallized. The product crystals were recrystallized from petroleum, giving colorless needles of fenchane-2,2'-spiro[2H-2,1b]naphthopyran. The product had a melting point of 105° C. The aforesaid naphthospiropyran in toluene exhibits a reversible change from colorless to yellow on exposure to the flash from a flash gun or unfiltered sunlight. The yellow color faded thermally at ambient temperatures in the absence of activating radiation.

EXAMPLE 2

Following the procedure of Example 1, the alcohol, 2-ethynyl-2-fenchol (17.8 grams, 0.1 mole), and 1-naphthol (14.4 grams, 0.1 mole) were dissolved in xylene (70 cc). One drop of concentrated sulfuric acid was added to the xylene solution, which was boiled under reflux for three hours. The reaction mixture was cooled and washed sequentially with a dilute (10 percent) sodium hydroxide solution and water. The organic layer was separated, diluted with diethyl ether (100 cc), dried over anhydrous magnesium sulfate, and filtered. Ether solvent was removed and the residual oil was chromatographed on silica gel using petroleum (b.p. 60°–80° C.) as the eluant. The photochromic fraction in the eluate was collected and the solvent removed. On standing, the residual colorless oil crystallized. The product crystals were recrystallized from petroleum, giving crystals of fenchane-2,2'-spiro[2H-1,2b] naphthopyran. The product had a melting range of 35°–37° C. The aforesaid naphthospiropyran in toluene exhibits a reversible change from colorless to orange on exposure to the flash from a flashgun or unfiltered sunlight. The orange color faded thermally at ambient temperature in the absence of activating radiation.

EXAMPLE 3

Following the procedure of Example 1, the alcohol, 2-ethynyl-2-fenchol (1.5 grams, 8.4 mmole) and 4-phenyl-1-naphthol (2.2 grams, 10 mmole) were dissolved in toluene (70 cc). One drop of concentrated sulfuric acid catalyst was added to the toluene solution and the reaction mixture boiled under reflux for three hours. The reaction mixture was cooled and washed sequentially with a dilute (10 percent) sodium hydroxide solution and water. The organic layer was separated, diluted with diethyl ether (100 cc), dried over anhydrous magnesium sulfate and filtered. Ether solvent was removed and the residual oil was chromatographed on silica gel using petroleum (b.p. 60°–80° C.) as the eluant. The photochromic fraction in the eluate was collected and the solvent removed. On standing, the residual colorless oil crystallized. The product crystals were recrystallized from petroleum giving crystals of fenchane-2,2'-spiro[2H-1,2b]-6-phenyl naphthopyran. The product had a melting point of 131° C. The naphthospiropyran in toluene exhibits a reversible change from colorless to orange on exposure to the flash of a flash gun or unfiltered sunlight.

EXAMPLE 4

Lithium acetylide/ethylene diamine complex (5 grams, 54 mmole) was added in small portions over 10 minutes to a solution of camphor (8.2 grams, 54 mmole) in 50 cc of dimethyl sulfoxide at room temperature. When the reaction was completed, the reaction mixture was poured onto crushed ice and acidified with dilute hydrochloric acid. The organic reaction product was extracted with diethyl ether (2×100 cc) and the resulting organic layer separated, dried over anhydrous magnesium sulfate and filtered. The filtrate was evaporated leaving the alcohol, 2-ethynyl-2-hydroxycamphor, in near quantitative yield. The product, an oil, crystallized on standing to form colorless needles.

Following the procedure of Example 2, the aforesaid alcohol, 2-ethynyl-2-hydroxycamphor (17.8 grams, 0.1 mole), and 1-naphthol (14.4 grams, 0.1 mole) were dissolved in toluene (70 cc). One drop of concentrated sulfuric acid catalyst was added to the toluene solution and the reaction mixture boiled under reflux for two hours. The reaction mixture was cooled and washed sequentially with a dilute (10 percent) aqueous sodium hydroxide solution and water. Using the work-up procedure described in Example 1 yielded a colorless oil which crystallized on standing. The crystal product was recrystallized from petroleum giving colorless needle crystals of the naphthospiropyran, camphane-2,2'-spiro-[2H-2,1b] naphthopyran, which had a melting point of 108° C. The aforesaid naphthospiropyran in toluene changed from colorless to yellow on exposure to the flash from a flashgun or unfiltered sunlight. The yellow color faded thermally at ambient temperatures in the absence of activating radiation.

EXAMPLE 5

Following the procedure of Example 4, the alcohol, 2-ethynyl-2-hydroxycamphor (17.8 grams. 0.1 mole) and 1-naphthol (14.4 grams 0.1 mole) were dissolved in toluene (70 cc). One drop of concentrated sulfuric acid catalyst was added to the toluene solution and the reaction mixture boiled under reflux for two hours. The reaction mixture was cooled and washed sequentially with a dilute (10 percent) aqueous sodium hydroxide solution and water Using the work-up procedure described in Example 1 yielded a colorless oil which crystallized on standing. The crystal product was recrystallized from petroleum giving pale yellow needles of the naphthospiropyran, camphane-2,2'-spiro[2H-1,2b] naphthopyran, which had a melting point of 115° C. The aforesaid naphthospiropyran in toluene changed from colorless to orange on exposure from a flashgun or unfiltered sunlight. The orange color faded thermally at ambient temperatures in the absence of activating radiation.

EXAMPLE 6

Following the procedure of Example 1, lithium acetylide/ethylene diamine complex (5 grams, 54 mmole) was added in small portions over 30 minutes to a solution of norcamphor (6.2 grams, 56 mmole) in dimethyl sulfoxide (50 cc). The reaction mixture was stirred at room temperature over the weekend. When the reaction was complete, the reaction mixture was poured onto crushed ice and acidified with dilute (10 percent) hydrochloric acid. The organic reaction product was extracted with diethyl ether, the ether extract separated, dried over anhydrous magnesium sulfate and filtered. The ether solvent was evaporated from the filtrate leaving as a colorless oil, the alcohol, 2ethynyl-2hydroxynorcamphor, in near quantitative yield. The oil crystallized on standing. The crystals had a melting point of 45° C.

The alcohol, 2ethynyl-2hydroxynorcamphor (6.8 grams, 50 mmoles), and 2naphthol (7.2 grams, 50 mmoles) were dissolved in toluene (50 cc). One drop of concentrated sulfuric acid catalyst was added to the toluene solution and the resulting reaction mixture boiled under reflux for 2 hours. The reaction mixture was cooled and washed sequentially with a dilute (10 percent) aqueous sodium hydroxide solution and water. Using the work-up procedure described in Example 1 yielded a brown oil which was chromatographed on silica gel using petroleum (b.p. 60°–80° C.) as the eluant. The photochromic fraction was separated and the petroleum solvent removed. The residual colorless oil crystallized on standing. The crystals were recrystallized from petroleum giving colorless crystal needles of the naphthospiropyran, norcamphane-2,2'-spiro[2H-2,1b]naphthopyran, which had a melting point of 68° C. The aforesaid naphthospiropyran product in toluene changed from colorless to yellow on exposure to the flash from a flashgun or unfiltered sunlight. The yellow color faded thermally in ambient temperatures in the absence of activating radiation.

EXAMPLE 7

Following the procedure of Example 1, the alcohol, 2-ethynyl-2-hydroxynorcamphor (6.8 grams, 50 mmoles) and 1-naphthol (7.2 grams, 50 mmole) were dissolved in toluene (50 cc). One drop of concentrated sulfuric acid was added to the toluene solution and the resulting reacting mixture boiled under reflux for two hours. The reaction mixture was cooled and washed sequentially with dilute (10 percent) aqueous sodium hydroxide and water, Using the work-up procedure of Example 1 gave a colorless oil containing the naphthospiropyran, norcamphane-2,2'-spiro[2H-1,2b]-naphthopyran. The aforesaid naphthospiropyran in toluene changed from colorless to orange on exposure to the flash from a flashgun and unfiltered sunlight. The orange color faded thermally at ambient temperatures in the absence of activating radiation.

EXAMPLE 8

Following the procedure of Example 1, the alcohol, 5-ethynyl-5-hydroxyoctahydro-4,7-methanoindine (10 grams, 57 mmoles), and 2-naphthol (12.27 grams, 85 mmoles) were dissolved in toluene (200 cc). A few drops of concentrated sulfuric acid were added to the hot toluene solution, which was boiled under reflux for 1 hour with removal of water using a Dean and Stark apparatus. Using the work-up procedure of Example 1, gave colorless crystals of the naphthospiropyran, octahydro-4',7'-methanoindene-5',2-spiro[2H,2,1b] naphthopyran.

The aforesaid naphthospiropyran in toluene changed from colorless to yellow on exposure to the flash of a flashgun and unfiltered sunlight. The yellow color faded thermally at ambient temperatures in the absence of activating radiation.

EXAMPLE 9

Following the procedure of Example 1, the alcohol, 5-ethynyl-5-hydroxyoctahydro-4,7-methanoindene (10 grams, 57mmoles), and 1-naphthol (12.27 grams, 85 mmoles) were dissolved in toluene (200 cc). A few drops of concentrated sulfuric acid were added to the hot solution, which was boiled under reflux for 1 hour with removal of water using a Dean and Stark apparatus. Using the work-up procedure of Example 1 gave as an oil the naphthospiropyran, octahydro-4',7'-methanoindeneas-5',2-spiro[2H,1,2b] naphthopyran.

The aforesaid naphthospiropyran in toluene changed from colorless to orange on exposure to the flash of a flashgun and unfiltered sunlight. The orange color faded thermally at ambient temperatures in the absence of activating radiation.

Although the present invention has been described with reference to specific details of certain embodiments thereof, it is not intended that such details should be regarded as limitations upon the scope of the invention except as and to the extent that they are included in the accompanying claims.

What is claimed is:

1. A compound represented by one of the following graphic formulae:

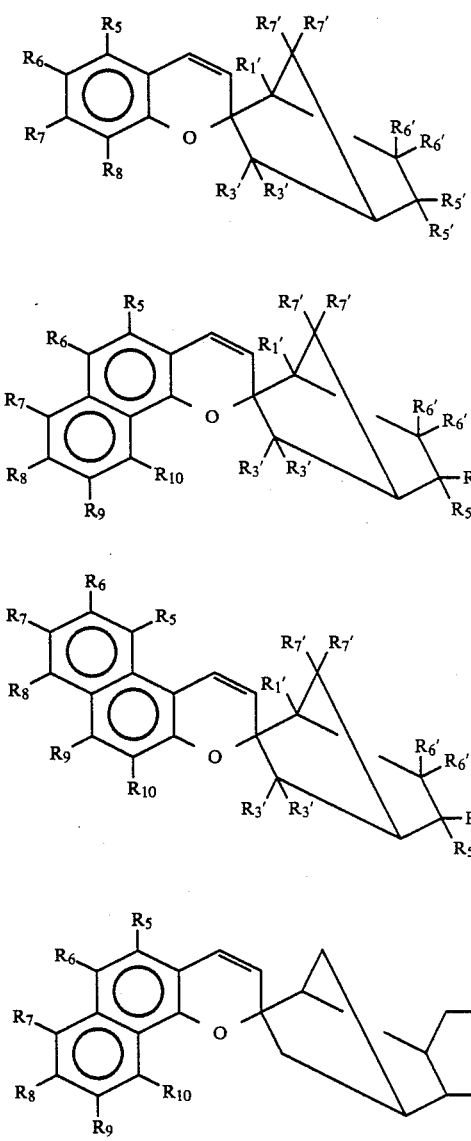

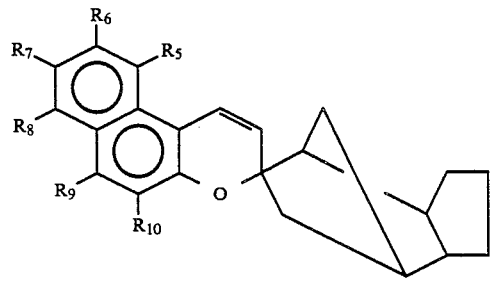

-continued wherein $R_5$-$R_{10}$ are each selected from the group consisting of hydrogen, $C_1$-$C_{10}$ alkyl, $C_5$-$C_7$ cycloalkyl, $C_1$-$C_4$ alkoxy, halogen, furyl, thienyl, phenyl, mono- and disubstituted phenyl, wherein the phenyl substituent is selected from the group consisting of $C_1$-$C_4$ alkyl, $C_1$-$C_4$ alkoxy, chloro and bromo, $R_1'$ and $R_3'$ are each selected from the group consisting of hydrogen and $C_1$-$C_5$ alkyl, and $R_5'$, $R_6'$ and $R_7'$ are each selected from the group consisting of hydrogen and methyl, provided that when $R_1'$ is hydrogen, $R_3'$, $R_5'$, $R_6'$ and $R_7'$ are each hydrogen and when $R_1'$ is alkyl, one of the $R_3'$, $R_5'$, $R_6'$ and $R_7'$ substituents is methyl, the other remaining substituents being hydrogen.

2. A compound according to claim 1 wherein $R_5$-$R_{10}$ are each selected from the group consisting of hydrogen, $C_1$-$C_5$ alkyl, $C_5$-$C_6$ cycloalkyl, $C_1$-$C_3$ alkoxy, phenyl, $C_1$-$C_4$ alkoxyphenyl, $C_1$-$C_4$ alkylphenyl, chlorophenyl, chloro and bromo and $R_1'$, $R_3'$, $R_5'$, $R_6'$ and $R_7'$ are each selected from the group consisting of hydrogen and methyl.

3. A naphthospiropyran compound according to claim 1 that may be represented by one of the following graphic formulae:

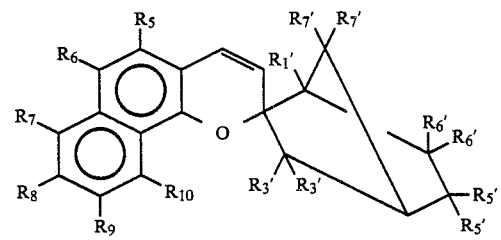

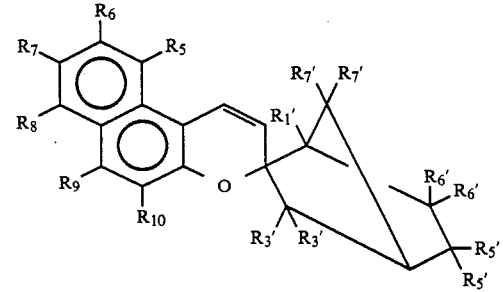

wherein $R_5$-$R_{10}$ are each selected from the group consisting of hydrogen, $C_1$-$C_3$ alkyl, $C_1$-$C_3$ alkoxy, chloro, bromo, phenyl, and $C_1$-$C_3$ alkoxyphenyl, and $R_1'$, $R_e'$, $R_5'$, $R_6'$ and $R_7'$ are each selected from the group consisting of hydrogen and methyl.

4. A compound of claim 3 wherein $R_6$-$R_{10}$ are hydrogen and $R_5$ is other than hydrogen.

5. A compound of claim 3 wherein $R_7$–$R_{10}$ are hydrogen and $R_5$ and $R_6$ are other than hydrogen.

6. A compound of claim 3 wherein $R_6$–$R_8$ and $R_{10}$ are hydrogen and $R_5$ and $R_9$ are other then hydrogen.

7. A compound of claim 4 wherein the $R_5$ substituent is selected from the group consisting of $C_1$–$C_3$ alkyl, $C_1$–$C_5$ alkoxy, $C_1$–$C_5$ alkoxyphenyl, chloro and bromo.

8. A compound of claim 5 wherein the $R_5$ and $R_6$ substituents are each selected from the group consisting of $C_1$–$C_5$ alkyl, $C_1$–$C_3$ alkoxy, $C_1$–$C_3$ alkoxyphenyl, chloro and bromo.

9. A compound of claim 6 wherein the $R_5$ and $R_9$ substituents are each selected from the group consisting of $C_1$–$C_3$ alkyl, $C_1$–$C_3$ alkoxy, $C_1$–$C_3$ alkoxyphenyl, chloro and bromo.

10. A photochromic article comprising a solid transparent polymerized organic host material and a photochromic amount of a photochromic compound represented by one of the graphic formulae:

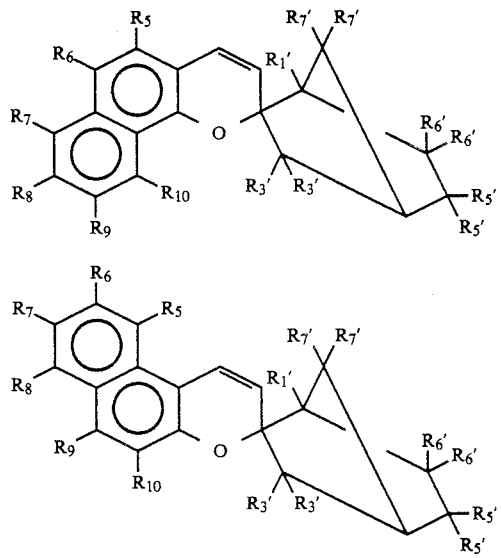

wherein $R_5$–$R_{10}$ are each selected from the group consisting of hydrogen, $C_1$–$C_{10}$ alkyl, $C_5$–$C_7$ cycloalkyl, $C_1$–$C_4$ alkoxy, halogen, furyl, thienyl, phenyl, mono- and disubstituted phenyl, wherein the phenyl substituent is selected from the group consisting of $C_1$–$C_4$ alkyl, $C_1$–$C_4$ alkoxy, chloro and bromo, $R_1'$ and $R_3'$ are each selected from the group consisting of hydrogen and $C_1$–$C_5$ alkyl, and $R_5'$, $R_6'$ and $R_7'$ are each selected from the group consisting of hydrogen and methyl, provided that when $R_1$ is hydrogen, $R_3'$, $R_5'$, $R_6'$, and $R_7'$ are each hydrogen, and when $R_1'$ is alkyl, one of the $R_3'$, $R_5'$, $R_6'$ and $R_7'$ substituents is methyl, the other remaining substituents being hydrogen.

11. The photochromic article cf claim 10 wherein $R_5$–$R_{10}$ are each selected from the group consisting cf hydrogen, $C_1$–$C_3$ alkyl, $C_1$–$C_3$ alkoxy, chloro, bromo, phenyl and $C_1$–$C_3$ alkoxyphenyl, and $R_1'$, $R_3'$, $R_5'$, $R_6'$ and $R_7'$ are each selected from the group consisting of hydrogen and 12. The photochromic article of claim 10 wherein the transparent polymerized organic host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

13. The photochromic article of claim 12 wherein the transparent polymerized organic host material is a homopolymer or copolymer of diethylene glycol bis(allyl carbonate).

14. The photochromic article of claim 13 wherein the photochromic compound is present in an amount of from 0.01 to 20 weight percent.

15. The photochromic article of claim 14 wherein the article is an optical element.

16. The photochromic article of claim 15 wherein the optical element is a lens.

17. A photochromic article comprising a solid transparent polymerized organic host material and a photochromic amount of each of (a) spirooxazine photochromic material selected from the group consisting of spiro(indolino) naphthoxazines and spiro(indolino) pyrido benzoxazines, and (b) photochromic material represented by one of the following graphic formulae:

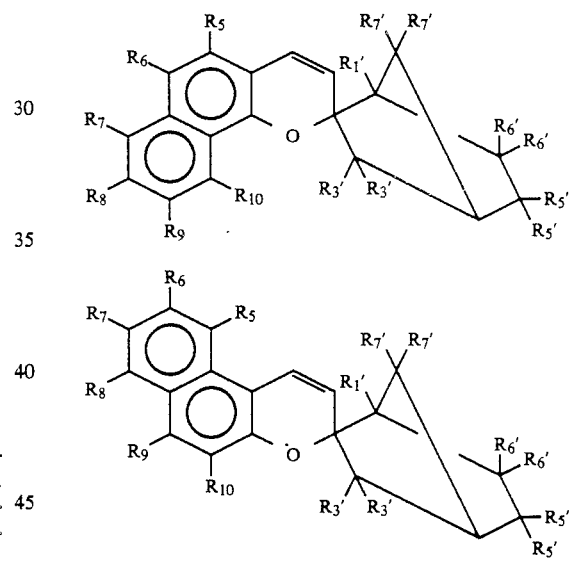

wherein $R_5$–$R_{10}$ are each selected from the group consisting of hydrogen, $C_1$–$C_5$ alkyl, $C_5$–$C_6$ cycloalkyl $C_1$–$C_3$ alkoxy, chloro, bromo, phenyl, $C_1$–$C_4$ alkoxyphenyl, $C_1$–$C_4$ alkylphenyl, and chlorophenyl, and $R_1'$, $R_3'$, $R_5'$, $R_6'$ and $R_4'$ are each selected from the group consisting of hydrogen and methyl, the mole ratio of photochromic material (a) to photochromic material (b) being from about 1:3 to about 3:1.

18. The photochromic article of claim 17 wherein the spiro(indolino) pyrido benzoxazine is represented by the graphic formula:

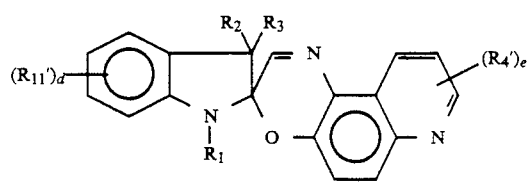

wherein,
(a) $R_1$ is selected from the group consisting of $C_1$-$C_4$ alkyl, phenyl, benzyl, 1-naphth($C_1$-$C_2$)alkyl, carboxy($C_2$-$C_4$)alkyl, cyano($C_2$-$C_4$)alkyl, $C_1$-$C_4$ acyloxy($C_2$-$C_4$)alkyl, hydroxy($C_2$-$C_4$)alkyl and $(C_2H_4O)_m \cdot CH_3$, wherein m is a number of from 1 to 3,
(b) $R_2$ and $R_3$ are each selected from the group consisting of $C_1$-$C_5$ alkyl and phenyl,
(c) $R_4'$ is selected from the group consisting of $C_1$-$C_5$ alkyl, $C_1$-$C_5$ alkoxy and halogen, and the letter e is a number of from 0 to 1,
(d) each $R_{11}'$ is selected from the group consisting of $C_1$-$C_5$ alkyl, halogen, $C_1$-$C_5$ alkoxy, nitro, cyano, $C_1$-$C_4$ monohaloalkyl, $C_1$-$C_4$ polyhaloalkyl, $C_1$-$C_8$ alkoxycarbonyl and $C_1$-$C_4$ acyloxy, and the letter d is a number of from 0 to 4.

19. The photochromic article of claim 17 wherein the spiro(indolino) naphthoxazine is represented by the graphic formula:

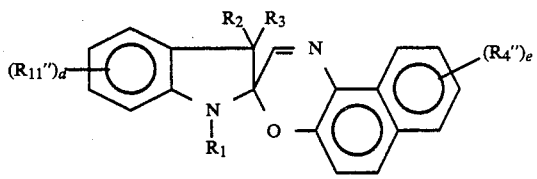

wherein,
(a) $R_1$ is selected from the group consisting of $C_1$-$C_4$ alkyl, phenyl, benzyl, 1-naphth($C_1$-$C_2$)alkyl, carboxy($C_2$-$C_4$)alkyl, cyano($C_2$-$C_4$)alkyl, $C_1$-$C_4$ acyloxy($C_2$-$C_4$)alkyl, hydroxy($C_2$-$C_4$)alkyl and $(C_2H_4O)_m \cdot CH_3$, wherein m is a number of from 1 to 3,
(b) $R_2$ and $R_3$ are each selected from the group consisting of $C_1$-$C_5$ alkyl and phenyl,
(c) each $R_4''$ is selected from the group consisting of halogen, $C_1$-$C_5$ alkyl, $C_1$-$C_5$ alkoxy, nitro, cyano, thiocyano, $C_1$-$C_4$ monohaloalkyl, $C_1$-$C_2$ polyhaloalkyl, mono($C_1$-$C_4$)alkylamino and di($C_1$-$C_4$)alkylamino, and the letter e is a number of from 0 to 2, and
(d) each $R_{11}''$ is selected from the group consisting of $C_1$-$C_5$ alkyl, halogen, $C_1$-$C_5$ alkoxy, nitro, cyano, $C_1$-$C_4$, monohaloalkyl, $C_1$-$C_4$ polyhaloalkyl, $C_1$-$C_8$ alkoxycarbonyl, $C_1$-$C_4$ acyloxy, and the letter d is a number of from 0 to 4.

20. The photochromic article of claim 17 wherein the transparent polymerized host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate). polystyrene, copoly(styrene-methylmethacrylate), copoly(styrene-acrylonitrile), polyvinylbutyral, and polymers of diallylidene pentaerythritol.

21. The photochromic article of claim 18 wherein the transparent polymerized host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

22. The photochromic article of claim 20 wherein the host material is prepared from homopolymers and copolymers of diethylene glycol bis(allyl carbonate).

23. The photochromic article of claim 21 wherein the host material is prepared from homopolymers and copolymers of diethylene glycol bis(allyl carbonate).

24. The photochromic article of claim 22 wherein the photochromic compounds are each present in amounts of from about 0.05 to about 10 weight percent.

25. The photochromic article of claim 23 wherein the photochromic compounds are each present in amounts of from about 0.05 to about 10 weight percent.

26. The photochromic article of claim 24 wherein the photochromic article is an optical element.

27. The photochromic article of claim 56 wherein the photochromic article is an optical element.

28. The photochromic article of claim 25 wherein the photochromic article is an ophthalmic lens.

29. A naphthospiropyran compound according to claim 1 that may be represented by the following graphic formula:

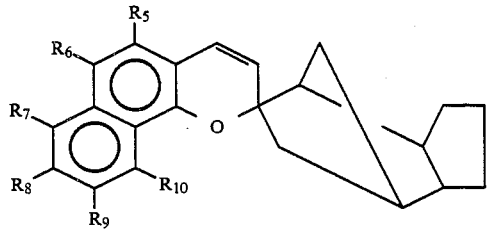

wherein (a) $R_6$-$R_{10}$ are hydrogen and $R_5$ is other than hydrogen, or (b) $R_6$-$R_8$ and $R_{10}$ are hydrogen, and $R_5$ and $R_9$ are other than hydrogen.

30. A naphthospiropyran according to claim 29 wherein the $R_5$ and $R_9$ substituents are each selected from the group consisting of $C_1$-$C_3$ alkyl, $C_1$-$C_3$ alkoxy, chloro and bromo.

* * * * *

UNITED STATES PATENT AND TRADEMARK OFFICE
CERTIFICATE OF CORRECTION

PATENT NO. : 4,980,089

DATED : December 25, 1990

INVENTOR(S) : Harry G. Heller

It is certified that error appears in the above-identified patent and that said Letters Patent is hereby corrected as shown below:

Claim 6, Column 27, line 4, "then" should be --than--.

Claim 7, Column 27, line 7, "$C_1$-$C_5$ alkoxy, $C_1$-$C_5$ alkoxyphenyl" should be --$C_1$-$C_3$ alkoxy, $C_1$-$C_3$ alkoxyphenyl--.

Claim 8, Column 27, line 10, "$C_1$-$C_5$ alkyl" should be --$C_1$-$C_3$ alkyl--.

Claim 11, Column 27, line 61, "hydrogen and" should be --hydrogen and methyl.--

Claim 17, Column 28, line 53, "$R_4$'" should be --$R_7$'--.

Claim 27, Column 30, line 33, "Claim 56" should be --claim 25--.

Signed and Sealed this

Twelfth Day of May, 1992

Attest:

DOUGLAS B. COMER

Attesting Officer

Acting Commissioner of Patents and Trademarks